(12) United States Patent
Kirschman

(10) Patent No.: US 11,052,168 B2
(45) Date of Patent: Jul. 6, 2021

(54) AIR GERMICIDAL DEVICE

(71) Applicant: David Louis Kirschman, Dayton, OH (US)

(72) Inventor: David Louis Kirschman, Dayton, OH (US)

(73) Assignee: AEROBIOTIX, INC., Miamisburg, OH (US)

( * ) Notice: Subject to any disclaimer, the term of this patent is extended or adjusted under 35 U.S.C. 154(b) by 585 days.

(21) Appl. No.: 15/813,506

(22) Filed: Nov. 15, 2017

(65) Prior Publication Data

US 2018/0133355 A1     May 17, 2018

Related U.S. Application Data

(60) Provisional application No. 62/422,803, filed on Nov. 16, 2016.

(51) Int. Cl.
*A61L 9/20* (2006.01)
*A61L 9/18* (2006.01)
*F24F 3/16* (2021.01)
*A61L 2/08* (2006.01)
*A61L 2/00* (2006.01)

(52) U.S. Cl.
CPC ............. *A61L 9/20* (2013.01); *A61L 2/0023* (2013.01); *A61L 2/08* (2013.01); *A61L 9/18* (2013.01); *A61L 2202/122* (2013.01); *A61L 2209/12* (2013.01)

(58) Field of Classification Search
CPC .................. A61L 9/18; A61L 9/20; F24F 3/16
See application file for complete search history.

(56) References Cited

U.S. PATENT DOCUMENTS

| | | | |
|---|---|---|---|
| 3,744,216 A | 7/1973 | Halloran | |
| 3,812,370 A | 5/1974 | LaViolette | |
| 3,988,131 A | 10/1976 | Kanazawa et al. | |
| 4,118,191 A | 10/1978 | Bohnensieker | |
| 4,208,012 A * | 6/1980 | Dutcher | A61L 9/12 239/57 |
| 4,210,429 A | 7/1980 | Golstein | |
| 4,244,710 A | 1/1981 | Burger | |
| 4,621,195 A | 11/1986 | Larsson | |
| 4,694,179 A | 9/1987 | Lew et al. | |
| 4,737,140 A | 4/1988 | Lee et al. | |
| 4,737,173 A | 4/1988 | Kudirka et al. | |
| 4,749,385 A | 6/1988 | Brunner et al. | |
| 4,787,922 A | 11/1988 | Kulitz | |
| 4,900,344 A | 2/1990 | Lansing | |

(Continued)

FOREIGN PATENT DOCUMENTS

WO    2014093094 A2    6/2014
WO    2014190066 A1    11/2014

*Primary Examiner* — Kevin Joyner
(74) *Attorney, Agent, or Firm* — Jacox, Meckstroth & Jenkins

(57) ABSTRACT

An air germicidal treatment device and system for removing or eliminating unwanted pathogens or bacteria in an airstream is shown. The device or system has a removable irradiation chamber that divides an interior area of the device into an air pre-chamber area, an air post-chamber area and an irradiation area therebetween. The removable irradiation chamber is generally trapezoidal in shape and has end walls that are inclined with respect to an interior divider wall.

31 Claims, 14 Drawing Sheets

(56) References Cited

U.S. PATENT DOCUMENTS

| | | | |
|---|---|---|---|
| 4,954,320 A | 9/1990 | Birmingham et al. | |
| 5,225,167 A | 7/1993 | Wetzel | |
| 5,240,478 A | 8/1993 | Messina | |
| 5,399,319 A | 3/1995 | Schoenberger et al. | |
| 5,601,786 A | 2/1997 | Monagan | |
| 5,616,172 A | 4/1997 | Tuckerman et al. | |
| 5,656,242 A | 8/1997 | Morrow et al. | |
| 5,891,399 A | 4/1999 | Owesen | |
| 5,997,619 A | 12/1999 | Knuth et al. | |
| 6,264,888 B1 | 7/2001 | Palestro et al. | |
| 6,322,614 B1 | 11/2001 | Tillmans | |
| 6,613,277 B1 | 9/2003 | Monagan | |
| 7,251,953 B2 | 8/2007 | Wetzel et al. | |
| 7,531,141 B2 | 5/2009 | Descotes et al. | |
| 7,674,436 B1 | 3/2010 | Feldman et al. | |
| 8,236,236 B2 | 8/2012 | Gamer | |
| 8,252,099 B2 | 8/2012 | Worrilow | |
| 9,433,693 B2 | 9/2016 | Kirschman | |
| 9,457,119 B2 | 10/2016 | Kirschman | |
| 9,764,054 B2 | 9/2017 | Kirschman | |
| 2001/0048889 A1 | 12/2001 | Palestro et al. | |
| 2002/0144601 A1 | 10/2002 | Palestro et al. | |
| 2003/0012703 A1 | 1/2003 | Lee | |
| 2003/0146082 A1 | 8/2003 | Gibson et al. | |
| 2003/0217641 A1 | 11/2003 | Palestro et al. | |
| 2004/0020363 A1 | 2/2004 | LaFerriere et al. | |
| 2006/0177356 A1 | 8/2006 | Miller | |
| 2012/0282135 A1 | 11/2012 | Trapani | |
| 2013/0239803 A1* | 9/2013 | Palmer | F24F 3/166 95/22 |
| 2014/0157989 A1 | 6/2014 | Kirschman | |
| 2014/0348701 A1 | 11/2014 | Kirschman | |
| 2016/0000960 A1* | 1/2016 | Soares Pinheiro Lopes | A61L 9/20 422/121 |
| 2016/0263267 A1 | 9/2016 | Kirschman | |
| 2016/0263268 A1 | 9/2016 | Kirschman | |
| 2017/0128601 A1* | 5/2017 | DeCiccio | A61L 2/22 |
| 2017/0296691 A1 | 10/2017 | Kirschman | |

\* cited by examiner

AIR GERMICIDAL DEVICE

CROSS-REFERENCE TO RELATED APPLICATION

The present application claims priority to provisional U.S. Application Ser. No. 62/422,803 filed Nov. 16, 2016, to which Applicant claims the benefit of the earlier filing date. This provisional application is incorporated herein by reference and made a part hereof.

BACKGROUND OF THE INVENTION

1. Field of the Invention

This invention relates to an air germicidal device and, more particularly, a germicidal device having a removable irradiation chamber adapted and shaped to define a generally trapezoidally shaped irradiation chamber area as well as an air pre-chamber area with positive pressure and an air post-chamber area having a negative pressure.

2. Description of the Related Art

Multiple methods have been proposed to inactivate or remove potentially pathogenic organisms from indoor air. Airborne bacteria, viruses and fungi are the cause of tremendous global disease, human suffering and economic loss. The issue of airborne pathogens is growing worse with increasing population density in urban areas, the emergence of drug-resistant pathogens, and an increasing elderly population with vulnerability to airborne infection.

Methods to disinfect air include mechanical filtration, irradiation, and chemical application. Each method has its benefits and drawbacks. Mechanical filtration is limited to organisms of a certain size, and the filtration of tiny viruses is impractical. Chemical application is effective, but airborne sprays of disinfecting chemicals present health and environmental challenges which often outweigh potential benefit. Air irradiation holds the greatest potential for efficient broad-spectrum disinfection of large air volumes, while maintaining environmental safety.

Air irradiation presents significant challenges. In order for an air disinfection device to be practical, it needs to disinfect large volumes of air travelling at high velocity. Biocidal rates are directly proportional to radiation output and exposure time. Radiation output is limited by practical power limitations for residential devices. In general, the required radiation power is squared as air velocity is doubled, quickly requiring impractical radiation outputs. Exposure time is related to the velocity and linearity of the treated airstream. U.S. Pat. No. 9,457,119, a device is shown for increasing biocidal efficiency of an air-irradiation device by transiently lowering air velocity and linearity. This was achieved by running the airstream though an irradiation chamber filled with a multitude of randomly-oriented radiation and air permeable cylinders.

What is needed, therefore, is a system, device and method that improves over the prior art.

SUMMARY OF THE INVENTION

The present invention improves upon U.S. Pat. No. 9,457,119 in several important ways. In order for the irradiation chamber to be utilized in a practical commercial product, additional development was performed. In order to maintain even airflow through the irradiation chamber, two fans were utilized, one each on the air inlet and exhaust. A single inlet fan creates a relative high pressure zone on the inlet side, resulting in an undesirable concentration of microbes in this location. Additionally, due to concerns about radiation leakage, a shielded pre-chamber and post-chamber were incorporated. In order to ensure adequate air dispersal in the irradiation chamber, a central spar was placed in the chamber, forcing the air to travel in a U-shaped pattern through the chamber, maximizing exposure to the cylinders. Finally, due to the desire for odor control in such a system, a layer of photocatalytic material is placed on the internal surfaces of the chamber to allow for radiation-induced oxidation of long-chain carbon compounds.

The features of the embodiments described herein may be used alone or in combination with the features of the embodiments shown and described in U.S. Pat. Nos. 9,433,693; 9,457,119; 9,764,054 and U.S. Patent Publication Nos. 2016/0263267 and 2017/0296691, all of which are incorporated herein by reference and made a part hereof.

A primary object of the invention is to provide an air germicidal device that is adapted to improve over the devices in the prior art.

Another object of the invention is to provide an air germicidal system and device having substantially even airflow through the device.

Another object of the invention is to provide an air germicidal device having an air pre-chamber area that is pressurized and an air post-chamber area that is under negative pressure.

Still object of the invention is to provide a removable irradiation chamber that is generally trapezoidal in shape and is situated between the air pre-chamber area and the air post-chamber area.

Yet another object of the invention is to provide an air treatment device and system that comprises means for reducing velocity of the air flowing through the device or system and increases irradiation time and efficiency of the air passing through the system or device.

Another object of the invention is to provide an air treatment device and system that is adapted and configured to provide a substantially even or constant airflow through an irradiation chamber of the device or system.

Yet another object of the invention is to provide an air treatment device that is portable and easily situated in a room where it is desired to treat or disinfect the air in the room.

In one aspect, one embodiment of the invention comprises an irradiation chamber for use in a germicidal device comprising a chamber housing defining a primary chamber; at least one spar or deflector situated in said chamber housing for increasing a length of an air pathway through the irradiation chamber.

In another aspect, one embodiment of the invention comprises a germicidal device comprising a device housing; a removable irradiation chamber; means for reducing velocity and linearity of air flowing through said removable irradiation chamber; at least one airflow generator for creating an airstream through said germicidal device; and a germicidal irradiation source for inactivating airborne microbes and unwanted bacteria in said airstream.

In still another aspect, one embodiment of the invention comprises a germicidal treatment system comprising a housing; an irradiation source; an irradiation chamber that is sized and adapted to be removable mounted in said housing, said irradiation chamber cooperating with said housing to define an air pre-chamber and an air post-chamber, said irradiation chamber having an inlet opening, an outlet opening and an irradiation opening that becomes operatively associated with said irradiation source in order to receive radiation from said irradiation source; a first airflow generator mounted on said housing and adapted to generate a positive pressure in said air pre-chamber and for introducing airflow from said air pre-chamber to said inlet opening; and a second airflow generator mounted on said housing and adapted to generate a negative pressure in said air post-chamber and for permitting said airflow to exit said outlet opening and into said air post-chamber.

In yet another aspect, one embodiment of the invention comprises a germicidal device which utilizes a germicidal irradiation source for the inactivation of airborne microbes; a removable irradiation chamber with means for reducing velocity and linearity of irradiated air; an air pre-chamber adapted to prevent radiation leakage from said chamber; an air post-chamber adapted to prevent radiation leakage from said chamber; an intake fan creating a relative high air pressure in said air pre-chamber; and an exhaust fan creating a relative vacuum in said air post-chamber.

In still another aspect, one embodiment of the invention comprises an air irradiation chamber utilizing a shape to allow for air ingress and egress with minimal air resistance; a central spar for increasing the length air pathway through said air irradiation chamber; and a means for reducing air velocity and linearity.

This invention, including all embodiments shown and described herein, could be used alone or together and/or in combination with one or more of the features covered by one or more of the following list of features:

The irradiation chamber wherein the chamber housing comprises a first wall and a generally opposing second wall, each of which are generally trapezoidal in shape and a first end wall and a second end wall coupling the ends of the first and second walls and being generally inclined relative to each other; the at least one spar or deflector being situated in the chamber housing to define a first chamber and a second chamber so that airflow is directed in a generally U-shaped path, the airflow passing into and through the first chamber in a first direction, around an edge of the at least one spar or deflector, and then into the second chamber where the airflow passes through the second chamber in a second direction that is generally opposite the first direction.

The irradiation chamber wherein the irradiation chamber comprises a reducer for reducing air velocity and linearity of the airflow as it passes through the irradiation chamber.

The irradiation chamber wherein the reducer comprises a plurality of multitude of discrete, randomly oriented and radiation-transmitting objects situated in at least one of the first chamber or the second chamber.

The germicidal device wherein the irradiation chamber is configured to define an air pre-chamber area adapted to facilitate preventing radiation leakage from the chamber and an air post-chamber area adapted to prevent radiation leakage from the chamber after the removable irradiation chamber is removable mounted in the device housing.

The germicidal device wherein the air pre-chamber and the air post-chamber are generally triangular.

The germicidal device wherein the air at least one airflow generator comprises a first airflow generator mounted in proximity to a first end of the device housing for creating a positive air pressure in the air pre-chamber and a second airflow generator mounted in proximity to a second end of the device housing for creating a negative pressure in the post-chamber area.

The germicidal device wherein the germicidal irradiation source is ultraviolet radiation.

The germicidal device wherein the means for reducing velocity and linearity comprises at least one spar or deflector being situated in a chamber housing to define a first chamber and a second chamber so that airflow is directed in a generally U-shaped path, the airflow passing into and through the first chamber in a first direction, around an edge of the at least one spar or deflector, and then into the second chamber where the airflow passes through the second chamber in a second direction that is generally opposite the first direction.

The germicidal device wherein the irradiation chamber comprises a reducer for reducing air velocity and linearity of the airflow as it passes through the irradiation chamber.

The germicidal device wherein the reducer comprises a plurality of multitude of discrete, randomly oriented and radiation-transmitting objects situated in at least one of the first chamber or the second chamber.

The germicidal device wherein the device housing comprises a first wall and a generally opposing second wall, each of which are generally trapezoidal in shape, a first end wall and a second end wall coupling the ends of the first and second walls to define an irradiation chamber, the generally opposing first and second walls being generally inclined relative to each other.

The germicidal device wherein the irradiation chamber comprises at least one spar or divider that divides the irradiation chamber to provide a first chamber area, a second chamber area and a joining area for joining the first and second chamber areas, the first and second chamber areas and the joining area cooperating to define a generally U-shaped or V-shaped airflow passageway.

The germicidal device wherein the irradiation chamber comprises at least one spar or divider that divides the irradiation chamber to provide a first chamber area for receiving airflow from the at least one airflow generator, a second chamber area and a joining area for joining the first and second chamber areas, the first and second chamber areas and the joining area cooperating to define a generally U-shaped or V-shaped airflow passageway.

The irradiation chamber wherein the joining area is operatively related and generally opposed to the germicidal irradiation source.

The irradiation chamber wherein the irradiation chamber is a one-piece construction and removable mounted in the germicidal device.

The germicidal treatment system wherein the air pre-chamber and the air post-chamber are generally triangular.

The germicidal treatment system wherein the first airflow generator is mounted in proximity to a first end of the housing for creating the positive air pressure in the air pre-chamber and the second airflow generator is mounted in proximity to a second end of the housing for creating the negative pressure in the air post-chamber.

The germicidal treatment system wherein the irradiation source is ultraviolet radiation.

The germicidal treatment system wherein the irradiation chamber comprises and irradiation chamber housing, the germicidal treatment system comprises at least one spar or divider situated in the chamber housing to define a first chamber and a second chamber so that airflow is directed in a generally U-shaped or V-shaped airflow passageway, the airflow passing into and through the first chamber in a first direction, around an edge of the at least one spar or deflector, and then into the second chamber where the airflow passes through the second chamber in a second direction that is not co-linear with the first direction.

The germicidal treatment system wherein the irradiation chamber comprises a reducer for reducing air velocity and linearity of the airflow as it passes through the irradiation chamber.

The germicidal treatment system wherein the reducer comprises a plurality of multitude of discrete, randomly oriented and radiation-transmitting objects situated in at least one of the first chamber or the second chamber.

The germicidal treatment system wherein the irradiation chamber housing comprises a first wall and a generally opposing second wall, each of which are generally trapezoidal in shape, a first end wall and a second end wall coupling the ends of the first and second walls to define an irradiation chamber, the generally opposing first and second walls being generally inclined relative to each other.

The germicidal treatment system wherein the at least one spar or divider divides the irradiation chamber to provide a first chamber area for receiving airflow from at least one airflow generator, a second chamber area and a joining area for joining the first and second chamber areas, the first and second chamber areas and the joining area cooperating to define the generally U-shaped or V-shaped airflow passageway.

The germicidal treatment system wherein the joining area is operatively related and generally opposed to the irradiation source.

The germicidal treatment system wherein the irradiation chamber is a one-piece construction and removable mounted in the germicidal treatment system.

The germicidal device wherein the air pre-chamber is substantially triangular.

The germicidal device wherein the air post-chamber is substantially triangular.

The germicidal device wherein the germicidal irradiation source is ultraviolet radiation.

The air irradiation chamber wherein the shape is substantially trapezoidal.

The air irradiation chamber wherein the means for reducing air velocity and linearity is a multitude of discrete, randomly oriented, radiation-transmitting objects.

These and other objects and advantages of the invention will be apparent from the following description, the accompanying drawings and the appended claims.

BRIEF DESCRIPTION OF THE ACCOMPANYING DRAWINGS

DETAILED DESCRIPTION OF THE PREFERRED EMBODIMENTS

Figure 1:
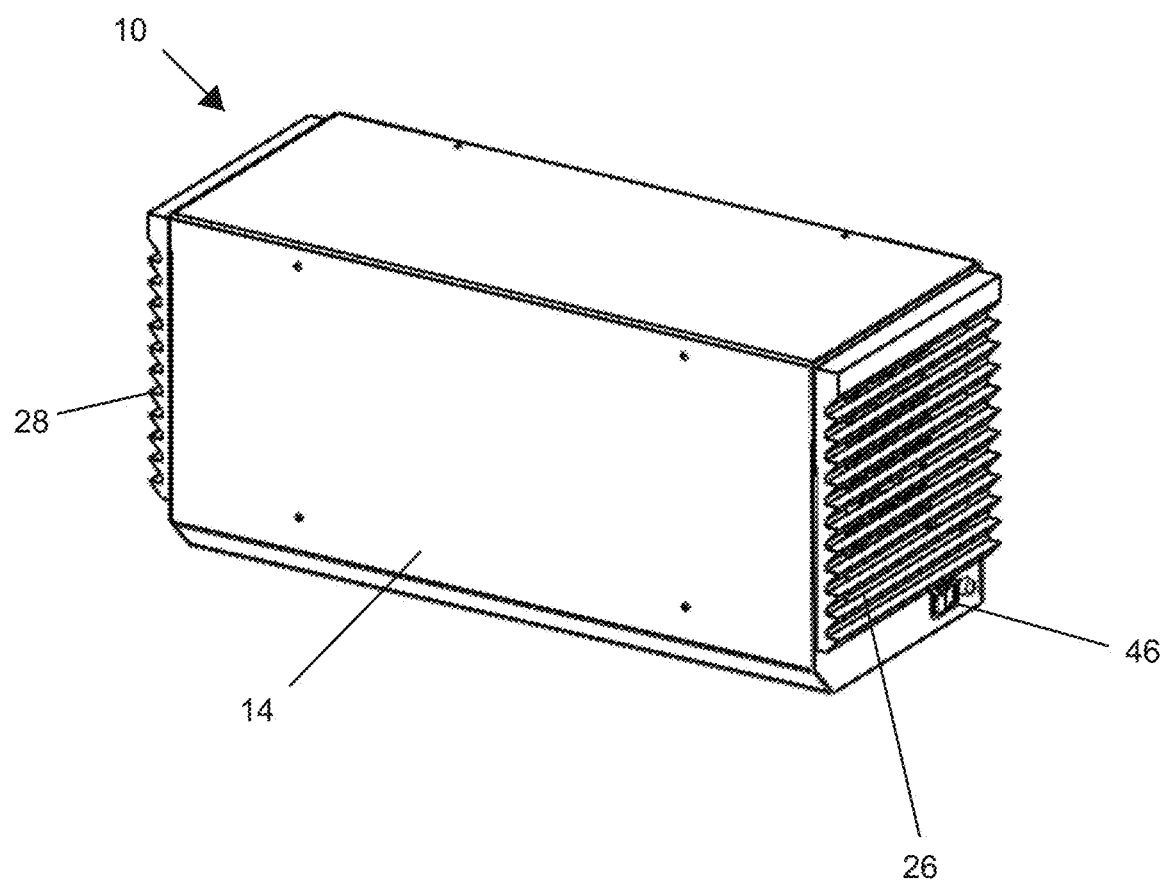
FIG. 1 is a perspective view of an assembled view of the air germicidal device and system in accordance with one embodiment.
Figure 2:
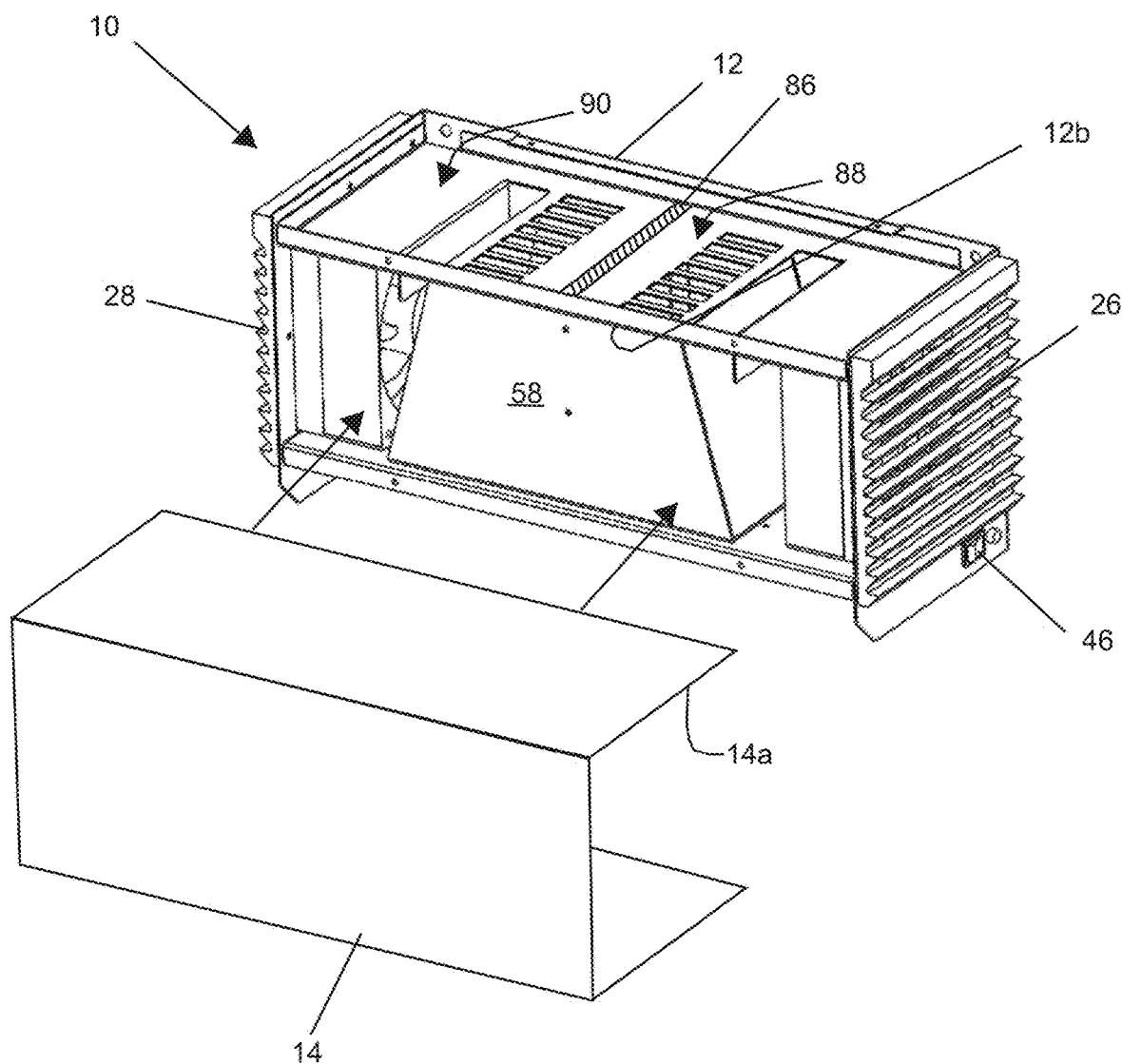
FIG. 2 is an exploded view of the device shown in FIG. 1 with a generally U-shaped cover removed.

Referring now to FIG. 1, a germicidal treatment device or system 10 is shown fully assembled. In the embodiments being described herein, the germicidal treatment device or system 10 is adapted to inactivate or remove potentially pathogenic organisms from indoor air. These organisms may include, but are not limited to, airborne bacteria, viruses and fungi. In general, the germicidal treatment device or system 10 is placed in an indoor area or room (not shown) in order to treat the air in the area or room.

Figure 3:
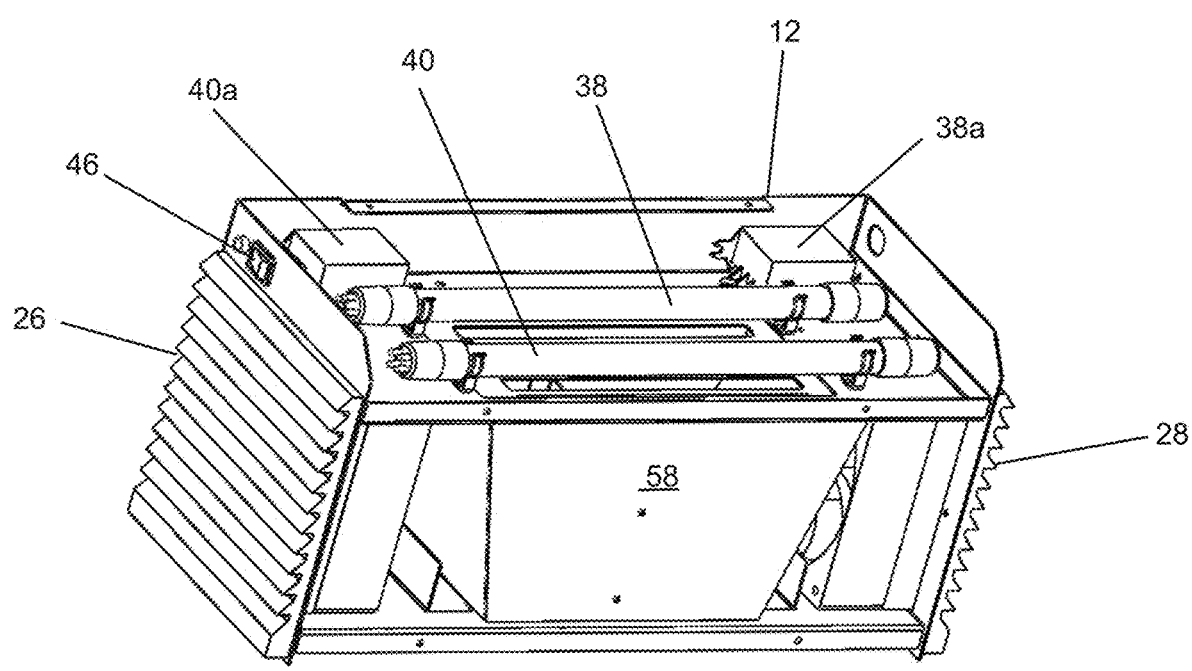
FIG. 3 shows various details of the components in the device shown in FIG. 1.
Figure 4:
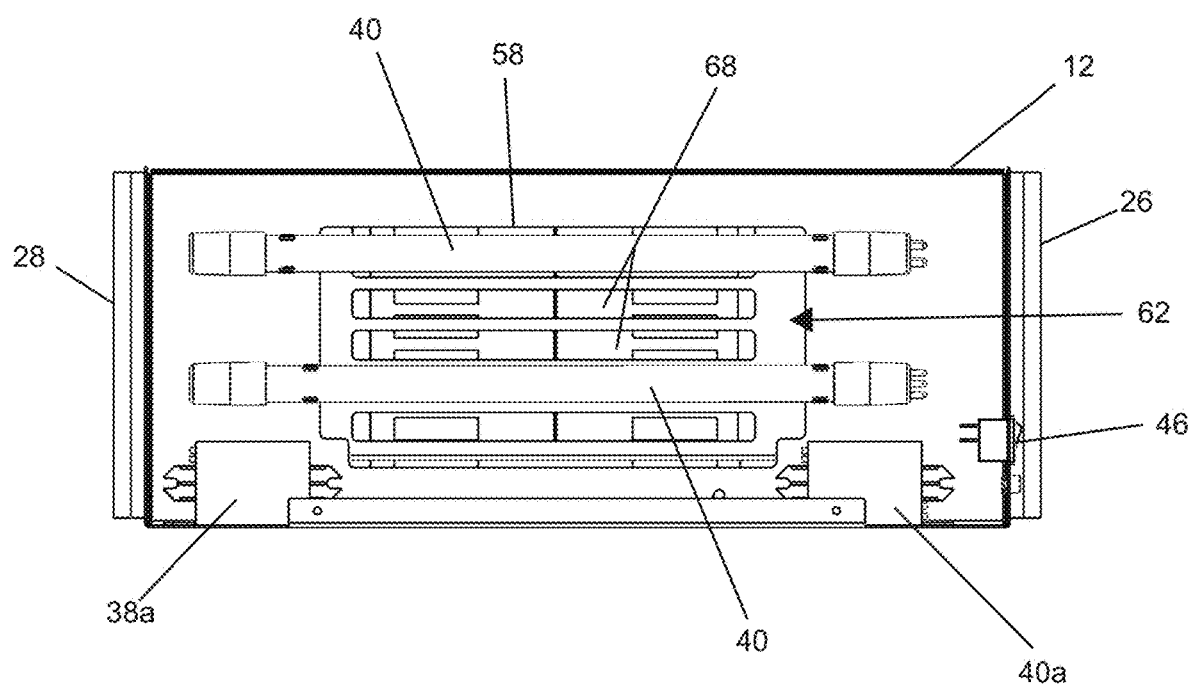
FIG. 4 is a bottom view, with cover removed, of the device shown in FIG. 1.
Figure 5:
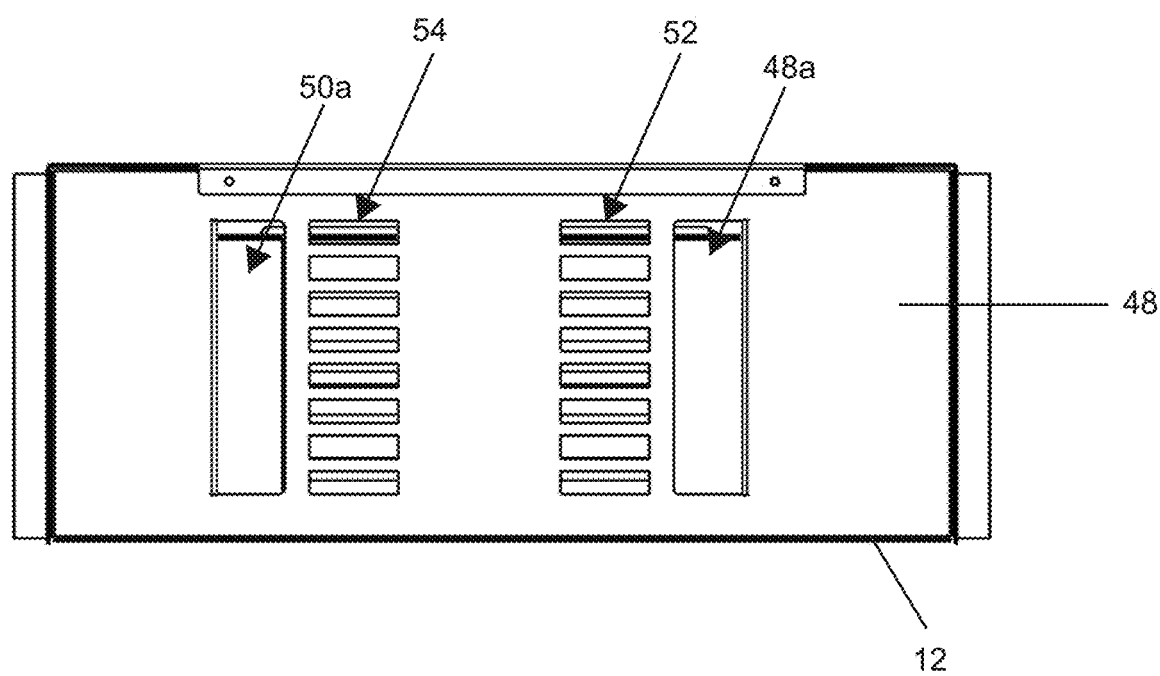
FIG. 5 is a plan view, with cover removed, of the device shown in FIG. 1.
Figure 6:
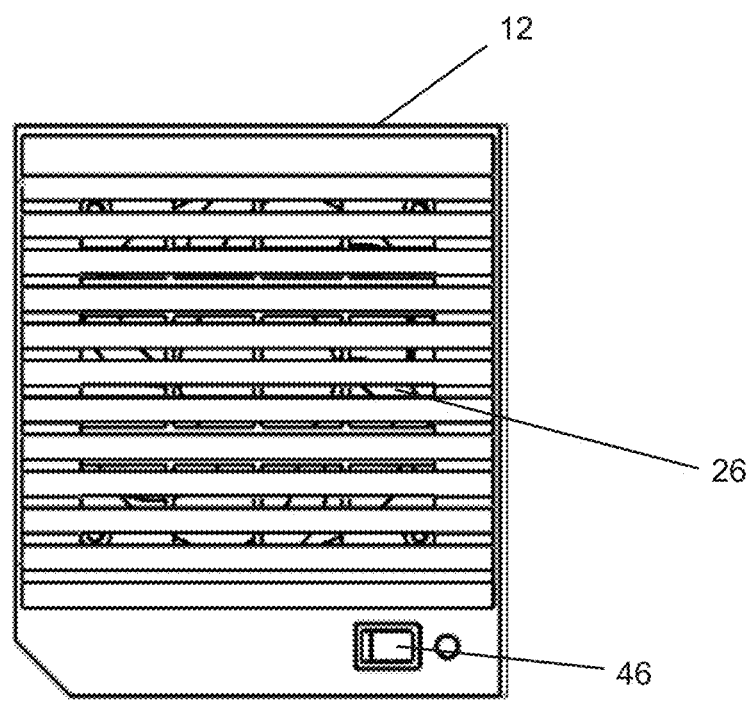
FIG. 6 is a right side view of the embodiment shown in FIG. 1.
Figure 7:
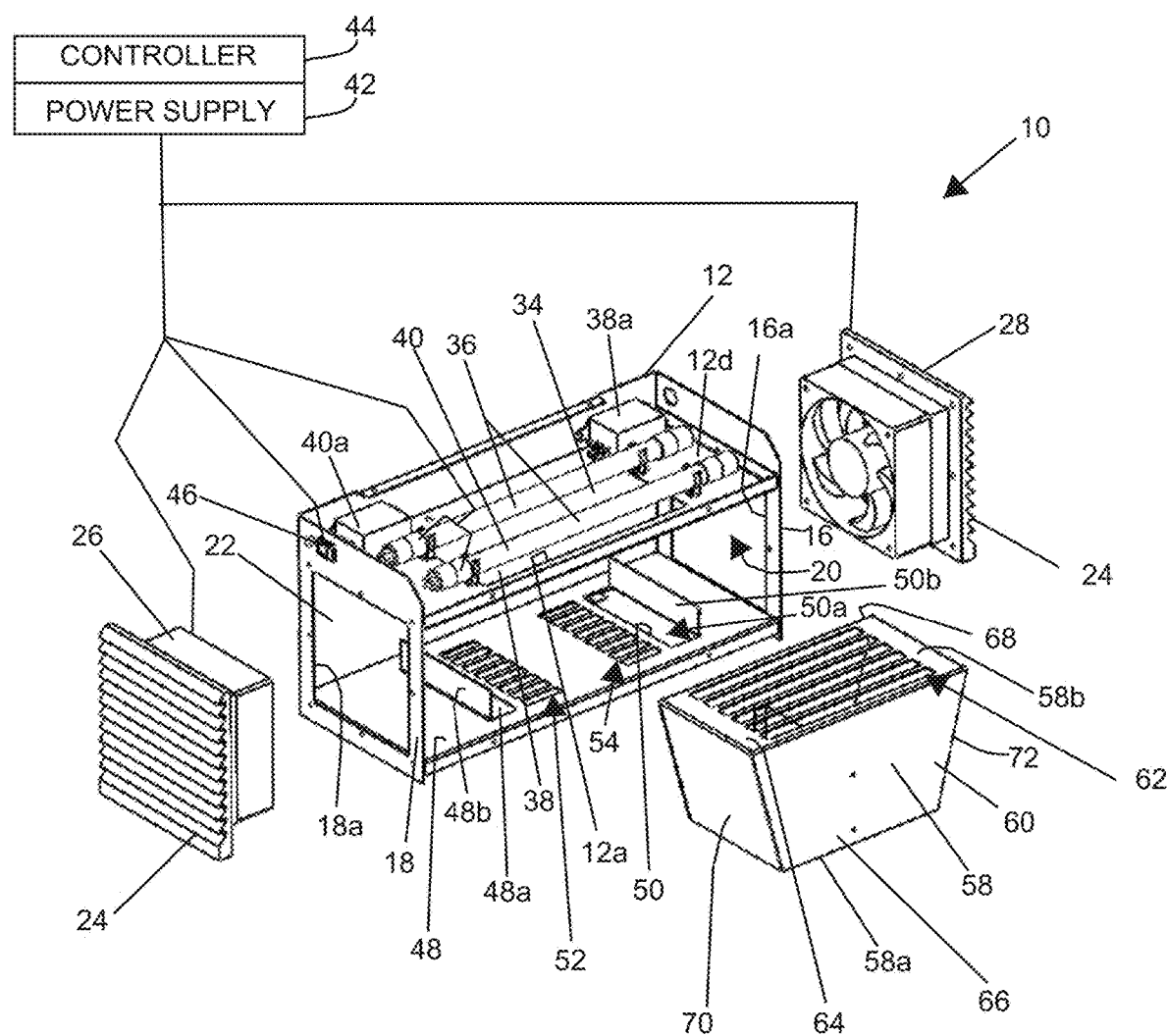
FIGS. 7-9 are exploded views showing various features of the embodiment shown in FIG. 1.
Figure 8:
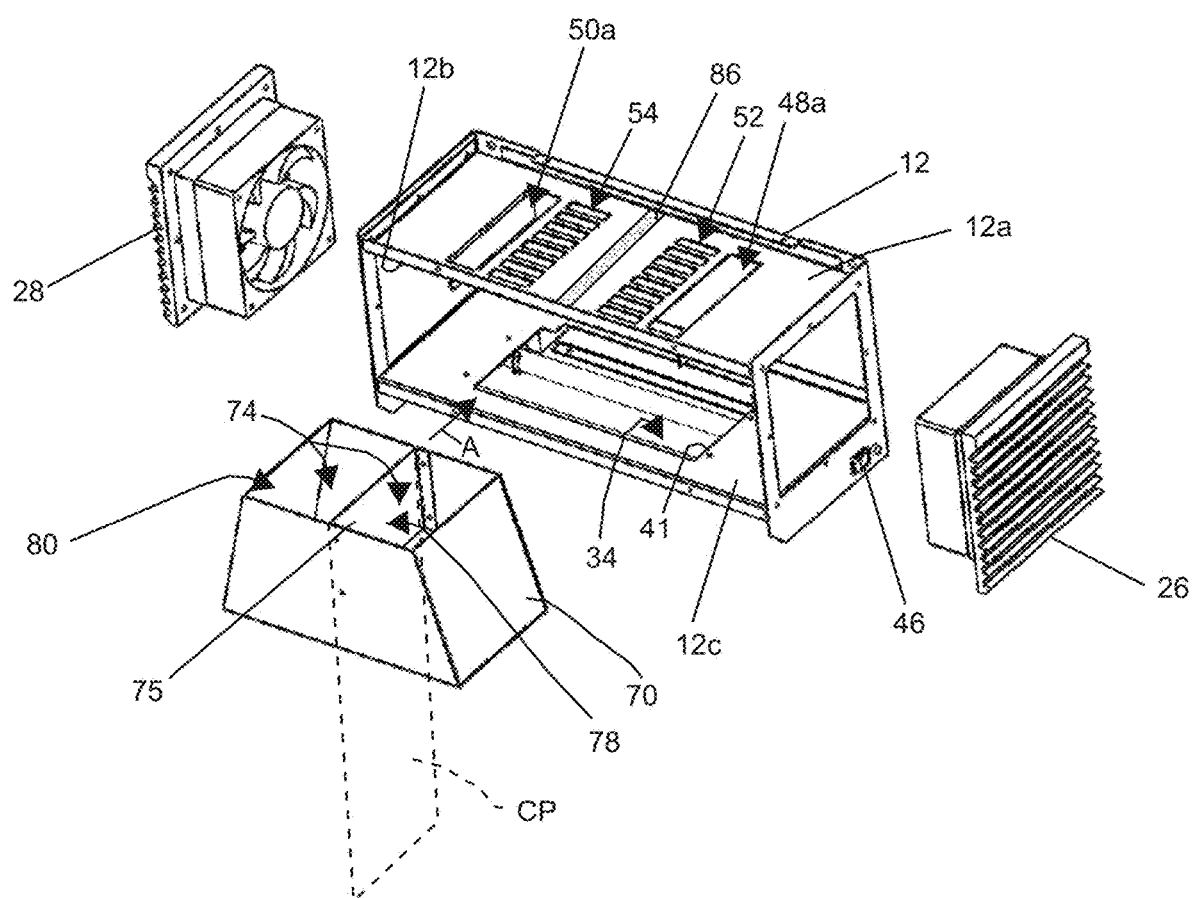
Figure 9:
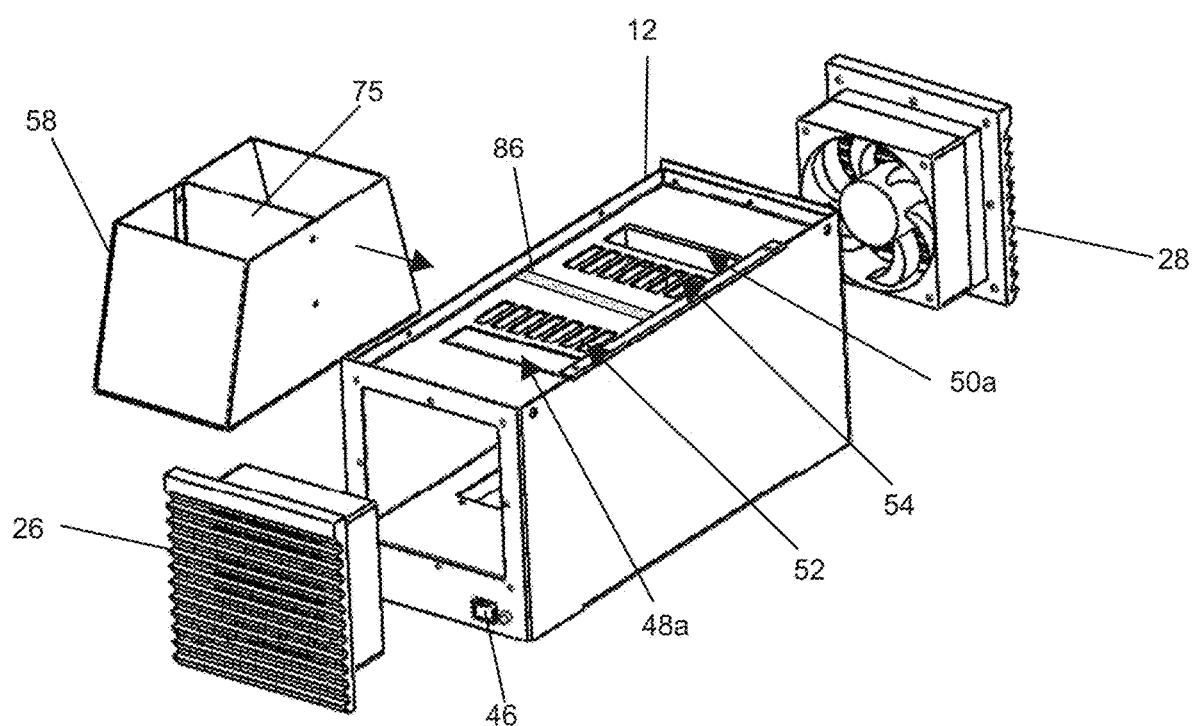
Figure 10:
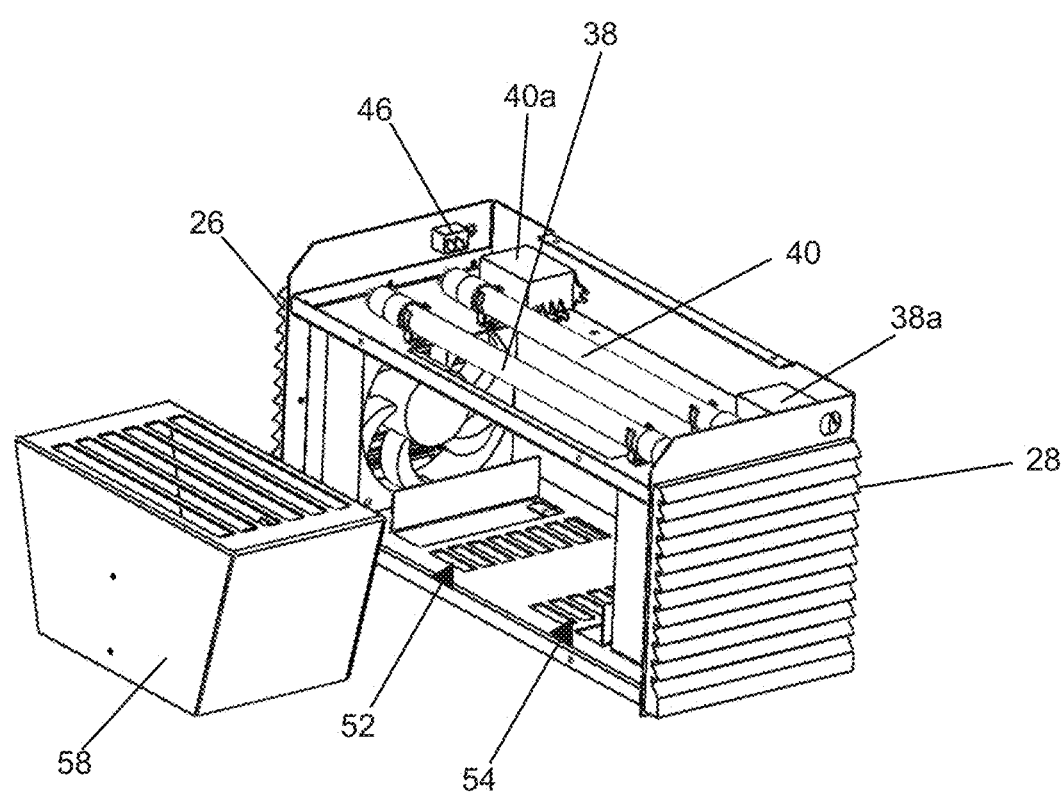
FIG. 10 is a view of the embodiment shown in FIG. 1 with the removable irradiation chamber removed from the device.
Figure 11:
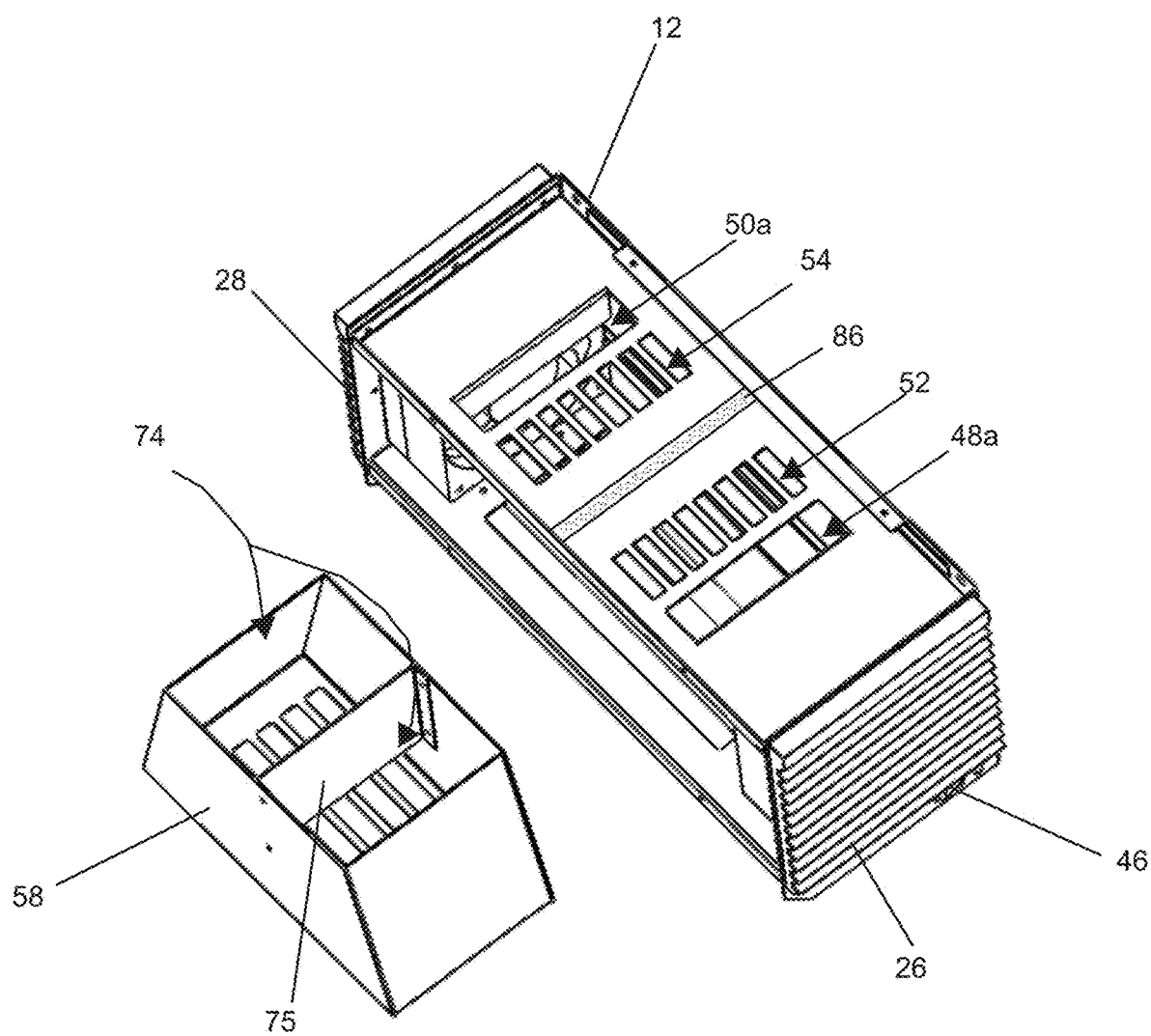
FIG. 11 is another view of the device shown in FIG. 1 with the cover housing removed and the irradiation chamber removed from the device showing a seal on a top surface of a frame of the device.

The germicidal treatment device or system 10 has a housing or frame 12, as illustrated in FIGS. 2-9, for supporting various components therein. A generally U-shaped housing cover 14 (FIG. 2) is mounted on the housing or frame 12 with conventional fasteners, such as screws (not shown), in order to protect the components therein. FIG. 3 and many of the other figures show various perspective and other views of the germicidal treatment device or system 10 with the housing or frame 12 removed. For example, FIG. 4 is a bottom view, FIG. 5 is a plan view and FIG. 6 is a right side view of the germicidal treatment device or system 10. The various components of the germicidal treatment device or system 10 will now be described relative to FIGS. 1-14. For ease of illustration and description, the description will proceed from the perspective view shown in FIG. 7. The housing or frame 12 comprises a first frame wall 16 having a first interior edge 16a and a second frame wall 18 that has an interior edge 18a. The interior edges 16a and 18a define apertures 20 and 22, respectively, each adapted and sized to receive at least one airflow generator 24.

Figure 12:
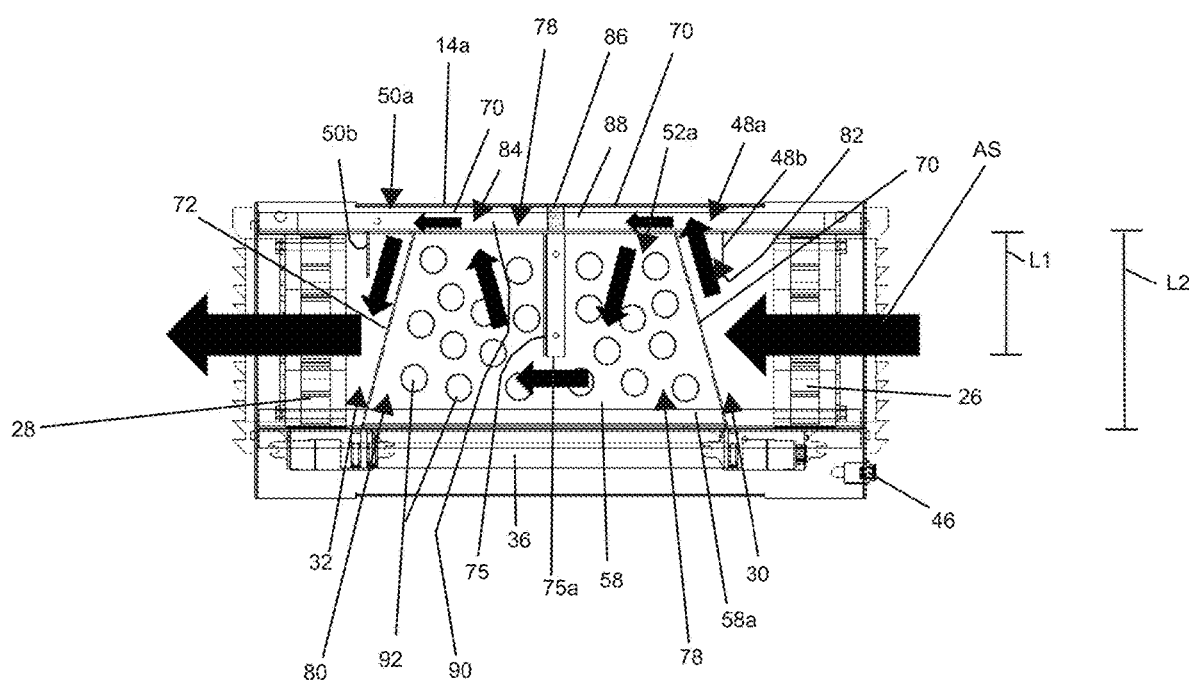
FIG. 12 is a view with the irradiation chamber situated in the device showing an airstream as it flows through the air pre-chamber area, into the irradiation chamber and through the air post-chamber area.

Thus, the germicidal treatment device or system 10 comprises at least one or a plurality of airflow generators 24 that are mounted in the apertures 20 and 22 on the housing or frame 12. In the illustration being described, the at least one or plurality of airflow generators 24 comprises a first airflow generator 26 and a second airflow generator 28 that are adapted and sized to be received in the apertures 20 and 22, respectively. In the illustration being described, the first airflow generator 26 is mounted to the housing or frame 12 and is adapted to generate a positive pressure in an air pre-chamber area 30 (FIG. 12). Likewise, the second airflow generator 28 is mounted on the housing or frame 12 and is adapted to generate a negative pressure in an air post-chamber area 32. The operation and flow of the airflow flowing through the germicidal treatment device or system 10 will be described later herein.

The housing or frame 12 comprises a wall 12d having an interior wall 41 (FIG. 8) that defines an irradiating aperture 34. As best illustrated in FIGS. 3, 4, 7 and 10, note that the germicidal treatment device or system 10 comprises an irradiation source 36 for inactivating airborne microbes and unwanted bacteria, viruses, fungi and the like from the airstream AS flowing past the aperture 34 and through the germicidal treatment device or system 10. In the illustration being described, the irradiation source 36 comprises at least one or a plurality of ultraviolet light sources 38 and 40 (FIG. 7) that have associated ballasts 38a and 40a that operate in a conventional manner. Any end caps or connectors between the first and second ultraviolet light sources 38 and 40 and a power supply 42 are not shown for ease of illustration.

The germicidal treatment device or system 10 comprises the power supply 42 and a controller 44 which are activated by a toggle switch 46. The controller 44 controls the operation of the germicidal treatment device or system 10. When the toggle switch 46 is actuated, the first and second airflow regulators 26 and 28 and the first and second ultraviolet light sources 38 and 40 are activated, thereby causing ultraviolet light to irradiate into and through the aperture 34 in order to disinfect the airstream AS flowing through the germicidal treatment device or system 10. This operation will be described later herein.

In the illustration being described, the housing or frame 12 is a stamped housing having a second interior wall 48 that generally opposes the surface or wall 41 and that defines a first aperture 48a and a second aperture 50a, each aperture 48a and 50a have an associated integral wall 48b and 50b, respectively that are generally perpendicular to the surface or wall 41. The housing or frame 12 further comprises a first plurality of apertures 52 and a second plurality of apertures 54, both of which define grates. In the illustration being described and as will be described later herein, the first plurality of apertures 52 permit air to flow from the air pre-chamber area 30 (FIG. 12) into a removable irradiation chamber 58.

In the illustration being described, the removable irradiation chamber 58 is sized and adapted to be removably mounted in the housing or frame 12. The removable irradiation chamber 58 comprises a wall 70 that cooperates with the housing or frame 12 and first airflow generator 26 to define the air pre-chamber area 30 and a wall 72 that cooperates with the frame 12 and second airflow generator 28 to define the air post-chamber area 32. Note that the removable irradiation chamber 58 comprises a housing 60 having a plurality of grates or apertures 62 in a wall or surface 64. The removable irradiation chamber 58 comprises a first side wall 66 and a generally opposing second side wall 68 as shown. The removable irradiation chamber 58 further comprises the first end wall 70 and the generally opposing second end wall 72. Note that the end walls 70 and 72 are coupled to the ends of the side walls 66 and 68 and are generally inclined relative to each other and relative to a central plane CP (shown in phantom in FIG. 8) of the removable irradiation chamber 58. The end walls 70 and 72 couple the ends of the side walls 66 and 68 to define an irradiation chamber area 74.

After the removable irradiation chamber 58 is removably received in the housing or frame 12, the grate or aperture 62 becomes operatively positioned relative to the aperture 34 and the irradiation source 36, namely the first and second ultraviolet light sources 38 and 40, so that ultraviolet irradiating light can pass through the aperture 34 and into the irradiation chamber 58 as will be described in more detail later herein.

Figure 13:
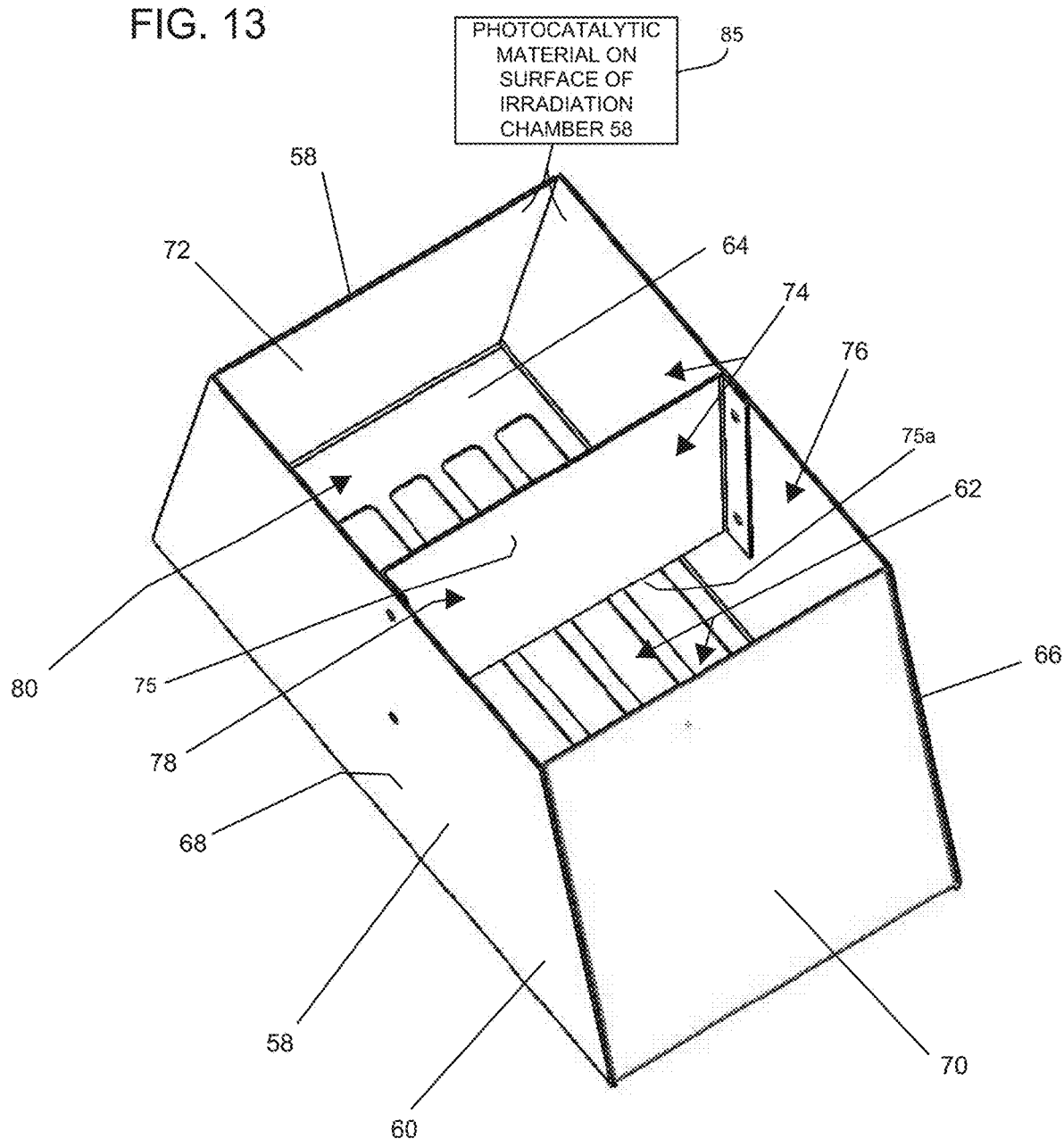
FIG. 13 is a view showing details of the removable irradiation chamber.

The irradiation chamber 58 comprises means for reducing velocity and increasing the time the airstream AS is exposed to radiation. In this regard, the irradiation chamber 58 comprises at least one spar, divider or deflector 75 that divides the chamber area 74 into a first chamber area 78 and a second chamber area 80 as best illustrated in FIG. 13. In the illustration being described, the irradiation chamber 58 is moved in the direction of arrow A in FIG. 8, whereupon the grates or apertures 52 and 54 of the housing or frame 12 become operatively associated with the irradiation chamber areas 78 and 80, respectively. Note also that the grate or aperture 62 on surface 64 becomes operatively associated with the opening or aperture 34 in the housing or frame 12.

After the first and second airflow generators 26 and 28 are conventionally mounted on the housing or frame 12 and secured thereto, the removable irradiation chamber 58 is removably mounted in the housing or frame 12. Thereafter, the cover 14 is mounted on the housing or frame 12 using conventional fasteners, such as screws.

FIG. 12 illustrates an airflow pattern and further features which will now be described. Note that after the irradiation chamber 58 is removably mounted in the housing or frame 12, the aperture 48a in a surface or wall 12a pf the housing or frame 12 becomes operatively associated with the wall 70 (FIG. 12) and wall 48b and defines an inlet passageway 82. Likewise, the wall 72 of the removable irradiation chamber 58 becomes operatively associated with the wall 50b and wall 72 and defines an exit passageway 84 into the air post-chamber area 32. When the first and second airflow generators 26 and 28 are energized by controller 44 and power supply 42 by actuation of the switch 46, the first airflow generator 26 generates a positive airflow pressure in the irradiation air pre-chamber area 30. The second airflow generator 28 also generates an airflow and a negative airflow pressure in the air post-chamber area 32. The first and second airflow generators 26 and 28 are axial fans in the illustration being described.

Note that an inner surface 14a (FIG. 2) of the cover 14 engages a foam gasket or seal 86 (FIGS. 2 and 9) which is mounted on the surface or wall 12a of the housing or frame 12.

When the first and second airflow generators 26 and 28 are energized, the air is pressurized and in the air pre-chamber area 30 and flows into and through the inlet passageway 82 and through the first aperture 48a into an airflow channel area or passageway 88 that is in communication with the plurality of grates or apertures 52. The air flows through the plurality of apertures 52 and into the first irradiation chamber area 78 and the air is forced past an end 75a (FIG. 12) of the spar, divider or deflector 75 wherein it then passes into and through the second air chamber area 80. The air flows through the plurality of grates or apertures 54 and into a second airflow channel or passageway 90 wherein it enters the second aperture 50a and into the air post-chamber area 32 whereupon it exits through the second airflow generator 28 to atmosphere. Note that the entire time that the air flows through the irradiation chamber 58, it is exposed to the ultraviolet radiation provided by the irradiation source 36, in this case the first and second fluorescent light sources 38 and 40. In the illustration being described, the spar, divider or deflector 75 causes the airflow to flow in a generally U-shape or V-shape path as illustrated in FIG. 12.

Advantageously, the design and shape of the irradiation chamber 58 facilitates reducing the air velocity of the air flowing through the germicidal treatment device or system 10 as well as reducing or changing the linearity of the airflow as it passes through the irradiation chamber 58. This in turn causes the airstream AS or airflow to be subjected to irradiation for a longer period of time compared to if the air flowed through the germicidal treatment device or system 10 linearly. This further has the benefit of increasing the effectiveness of the irradiation to kill unwanted pathogens or bacteria.

In order to further facilitate the effectiveness of the germicidal treatment device or system 10, the germicidal treatment device or system 10 may comprise one or more reducers for further reducing or disturbing the air velocity and linearity of the airflow as it passes through the irradiation chamber 58. In this regard, the at least one reducer may comprise a plurality or multitude of discrete, randomly oriented and radiation-transmitting objects or tubular members 92 (FIG. 14), like those used in U.S. Pat. Nos. 9,433,693; 9,457,119; 9,764,054 and U.S. Patent Publication Nos. 2016/0263267 and 2017/0296691, situated in at least one or both of the first irradiation chamber area 78 or second irradiation chamber 80. Note in FIG. 14 that the portion of the objects or tubular members 92 is random in FIG. 14, but they could be ordered if desired, which is shown in FIG. 12. The Additional Considerations Advantageously, the first and second axial fans or airflow generators 26 and 28 maintain an even airflow through the irradiation chamber 58. In contrast, the prior art oftentimes utilized a single inlet fan that created a relatively high pressure zone on an inlet side (not shown) of the device that resulted in an undesirable concentration of microbes in that location.

The removable irradiation chamber 58 becomes sealed in the housing or frame 12 which reduces or eliminates concerns about radiation leakage. removable irradiation chamber 58 comprises a first edge 58a which is generally rectangular and which engages the aperture 48a and engages or becomes sealed against the surface 12b (FIGS. 2 and 8) after the removable irradiation chamber 58 is mounted in the housing or frame 12. Likewise, the surface 58b engages and becomes sealed against the surface 12c (FIG. 8) of the housing or frame 12. It is important to note that the air pre-chamber area 30 and air post-chamber area 32 are shielded and sealed from the irradiation chamber 58. Note in the illustration being described and shown in FIG. 12, the air pre-chamber area 30 and air post-chamber area 32 are generally triangular as viewed from the side in FIG. 12 and, again, shielded from the radiation generated by the irradiation source 38.

Note as illustrated in FIG. 12, that the spar, divider or deflector 75 has a length L1 that is shorter than an overall length L2 of the irradiation chamber 58. This forces the air flowing into and through the irradiation chamber 58 to travel in a serpentine or the generally U-shaped or V-shaped pattern. This maximizes the exposure of the airstream AS to the irradiation source 38. It should be understood that the means for reducing the velocity of the air may include, but are not limited to, the at least one airflow interrupter, deflector and the other features of the irradiation chamber that are adapted to provide or define the serpentine or non-linear pathway.

There may be a desire for odor control in the germicidal treatment device or system 10, in which case a layer of photocatalytic material 85 (FIG. 13) may be placed on one or more of the interior surfaces of the irradiation chamber 58. The photocatalytic material 85 allows for radiation-induced oxidation of long-chain carbon compounds in a manner conventionally known.

It should be appreciated and as illustrated in the airflow diagram of FIG. 12, that the airflow path caused by the irradiation chamber 58 and the spar, divider or deflector 75 maximizes radiation exposure time and prevents leakage of ultraviolet energy through the intake and exhaust of the germicidal treatment device or system 10.

FIG. 5 illustrates a plan view of the germicidal treatment device or system 10 with the cover 14 removed showing the vents and various apertures 48a, 50a, 52 and 54 that allow air to enter and exit the irradiation chamber 58. FIG. 3 illustrates the irradiation chamber 58 positioned in the housing or frame 12 and showing the first and second irradiation light sources 38 and 40. Once the irradiation chamber 58 is positioned in the housing or frame 12 as shown, the cover 14 (FIG. 2) may be mounted on the housing or frame 12. FIG. 4 is a bottom view demonstrating the plurality of second irradiation light sources in operative relationship with the aperture 34 and the grate or aperture 62 of the removable irradiation chamber 58.

Figure 14:
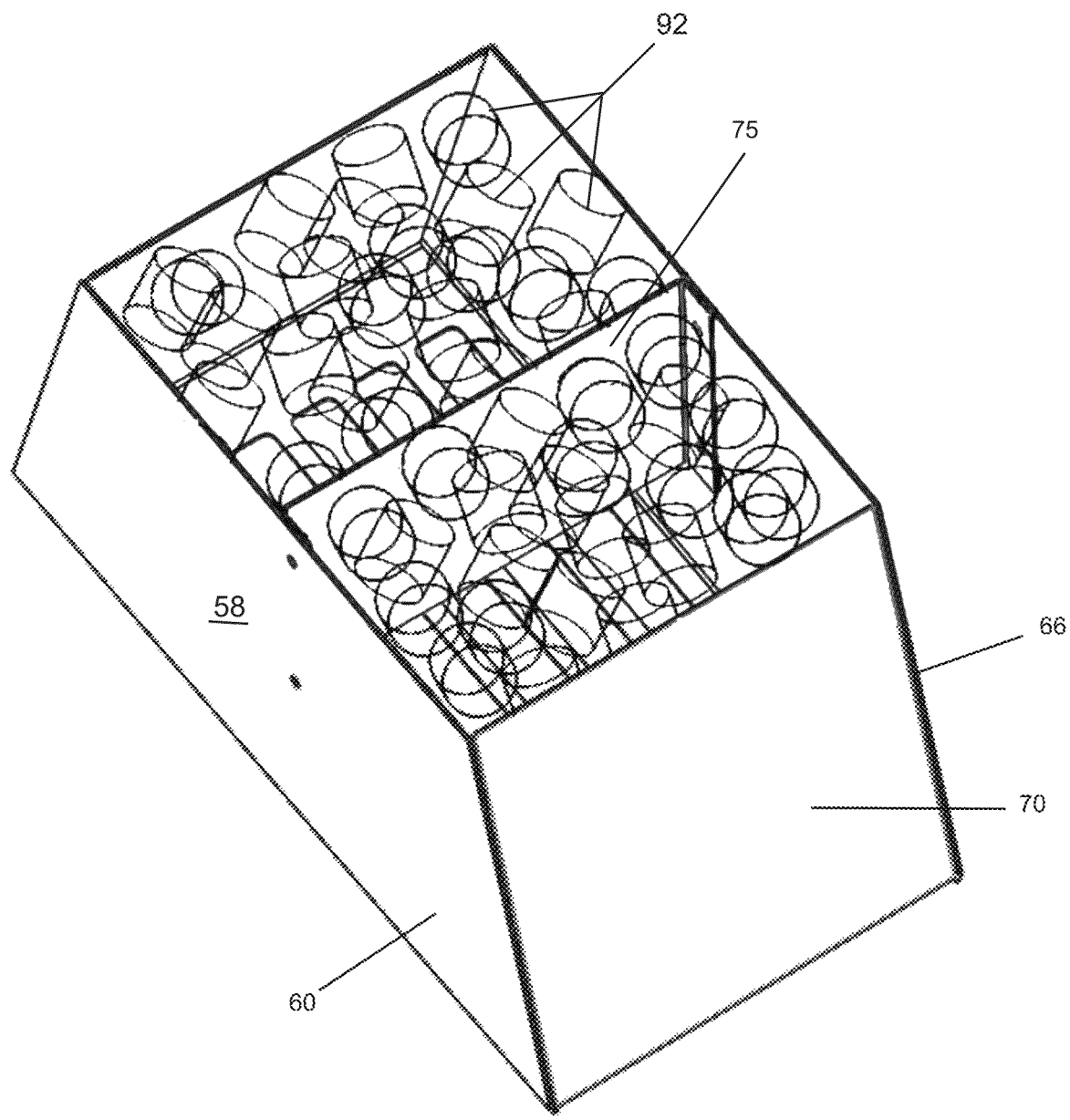
FIG. 14 is a view of the removable irradiation chamber showing a multitude or a plurality of randomly-oriented radiation and air permeable cylinders or tubular members.

In order for an air disinfection device to be practical, it needs to disinfect large volumes of air travelling at high velocity. Biocidal rates are directly proportional to radiation output and exposure time. Radiation output is limited by practical power limitations for residential devices. In general, the required radiation power is squared as air velocity is doubled, quickly requiring impractical radiation outputs. Exposure time is related to the velocity and linearity of the treated airstream. U.S. Pat. No. 9,457,119, which is assigned to the same Assignee as the present application, describes a device for increasing biocidal efficiency of an air-irradiation device by transiently lowering air velocity and linearity. This was achieved by running the airstream though an irradiation chamber filled with a multitude of randomly-oriented radiation and air permeable cylinders. These may be used in the embodiments described herein. The circular and rotatably-oriented tubular members 92 in FIGS. 12 and 14 illustrate this feature. Moreover, other features of the system or devices shown in U.S. Pat. Nos. 9,433,693; 9,457,119; 9,764,054 and U.S. Patent Publication Nos. 2016/0263267 and 2017/0296691, may be used in combination with features of the embodiments described herein, and those references are incorporated herein by reference and made a part hereof.

This invention, including all embodiments shown and described herein, could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:
1. A germicidal device comprising:
a housing;
a irradiation chamber for situating in said housing;
means for reducing velocity and linearity of air flowing through said irradiation chamber;
at least one airflow generator for creating an airstream through said germicidal device; and
a germicidal irradiation source for irradiating or inactivating airborne microbes and unwanted bacteria in said airstream;
wherein said irradiation chamber comprises a first wall and an opposing second wall, a first end wall, and a second end wall coupling said first and second walls, said first and second end walls being generally inclined relative to each other;

at least one spar or deflector situated in said irradiation chamber and defining a first chamber and a second chamber in said irradiation chamber so that airflow is directed in a generally U-shaped or serpentine path, said airflow passing into and through said first chamber in a first direction and then into said second chamber where said airflow passes through said second chamber in a second direction that is no co-linear with said first direction;

said germicidal irradiation source irradiating said airstream as it passes through both of said first and second chambers;

wherein said irradiation chamber is configured to cooperate with said housing to define an air pre-chamber area adapted to facilitate preventing radiation leakage from said air pre-chamber and an air post-chamber area adapted to prevent radiation leakage from said air post-chamber.

2. An irradiation chamber for use in a germicidal device according to claim 1, said germicidal device comprising:

a chamber housing defining a primary chamber;

at least one spar or deflector situated in said chamber housing for increasing a length of an air pathway through the irradiation chamber;

wherein said chamber housing comprises a first wall, an opposing second wall, a first end wall, and a second end wall, said first and second end walls coupling said first and second walls, said first and second end walls being generally inclined relative to each other;

said at least one spar or deflector being coupled to said chamber housing situated in said primary chamber to define a first chamber and a second chamber in said chamber housing so that airflow is directed in a generally U-shaped or serpentine path, said airflow passing into and through said first chamber in a first direction, past said at least one spar or deflector, and then into said second chamber where said airflow passes through said second chamber in a second direction that is not co-linear with said first direction.

3. The irradiation chamber as recited in claim 2, wherein said first end wall and said second end wall couple the ends of said first and second walls;

wherein a first fan is operatively associated with said first end wall which directs airflow from said first end wall in said first direction and toward said first chamber and a second fan operatively associated with said second wall which directs airflow from said second chamber and facilitate directing it out of said germicidal device;

said first fan creating a positive pressure in an air pre-chamber that is upstream of and in fluid communication with said first chamber and said second fan creating a negative pressure in an air post-chamber that is downstream from an pre-chamber, said first chamber and said second chamber.

4. The irradiation chamber as recited in claim 3 wherein said irradiation chamber comprises a reducer for reducing air velocity and linearity of said airflow as it passes through said irradiation chamber.

5. The irradiation chamber as recited in claim 4 wherein said reducer comprises a plurality of multitude of discrete, randomly oriented and radiation-transmitting objects situated in at least one of said first chamber or said second chamber.

6. The germicidal device as recited in claim 1 wherein said air pre-chamber and said air post-chamber are generally triangular when viewed in at least one cross-section.

7. The germicidal device as recited in claim 1 wherein said at least one airflow generator comprises a first airflow generator mounted in proximity to a first end of said housing for creating a positive air pressure in said air pre-chamber and a second airflow generator mounted in proximity to a second end of said housing for creating a negative pressure in said post-chamber area.

8. The germicidal device as recited in claim 1 wherein said germicidal irradiation source is ultraviolet radiation.

9. The germicidal device as recited in claim 1 wherein said first and second chambers cooperate to cause the air to flow in a generally U-shaped or V-shaped path, said airflow passing into and through said first chamber in a first direction, around an edge of said at least one spar or deflector, and then into said second chamber where said airflow passes through said second chamber in a second direction that is different from said first direction.

10. The germicidal device as recited in claim 9 wherein said means for reducing velocity comprises a reducer for reducing air velocity and linearity of said airflow as it passes through said irradiation chamber.

11. The germicidal device as recited in claim 10 wherein said reducer comprises a plurality of multitude of discrete, randomly oriented and radiation-transmitting objects situated in at least one of said first chamber or said second chamber.

12. The germicidal device as recited in claim 1 wherein said irradiation chamber comprises said first wall and said opposing second wall, each of which are generally trapezoidal in shape, said first end wall and said second end wall coupling the ends of said first and second walls to define a chamber, said opposing first and second end walls being generally inclined relative to each other.

13. The germicidal device as recited in claim 1 wherein said at least one spar or divider divides said irradiation chamber to provide said first chamber, said second chamber and a joining area for joining a first and a second area, said first and second chambers and said joining area cooperating to define said generally U-shaped or V-shaped airflow passageway.

14. The germicidal device as recited in claim 13 wherein said at least one spar or divider divides said irradiation chamber to provide said first chamber for receiving airflow from said at least one airflow generator, said second chamber and a joining area for joining said first and second chamber areas, said first and second chamber areas and said joining area cooperating to define said generally U-shaped or V-shaped airflow passageway.

15. The germicidal device as recited in claim 14 wherein said joining area is operatively related and generally opposed to said germicidal irradiation source.

16. The germicidal device as recited in claim 14 wherein said irradiation chamber is a one-piece construction and removable mounted in said germicidal device.

17. A germicidal treatment system of the germicidal device according to claim 1 wherein said at least one airflow generator comprises a first airflow generator and a second airflow generator, said first airflow generator being mounted on adapted to generate a positive pressure in said air pre-chamber and for introducing airflow from said air pre-chamber to an inlet opening; and said second airflow generator being mounted on said housing and adapted to generate a negative pressure in said air post-chamber and for permitting said airflow to exit an outlet opening and into said air post-chamber; wherein said irradiation chamber comprises said first end wall that is associated with said air pre-chamber and that is generally inclined to facilitate directing airflow from said first airflow generator and said pre-chamber toward a primary chamber of said irradiation chamber and said second end wall that is associated with said air post-chamber and that is generally inclined relative to said second chamber in order to receive airflow from said primary chamber and direct it into said air post-chamber after said airflow has passed through said air pre-chamber and said primary chamber.

18. The germicidal treatment system as recited in claim 17 wherein said air pre-chamber and said air post-chamber each have a shape in cross-section that is generally triangular.

19. The germicidal treatment system as recited in claim 17 wherein said first airflow generator is mounted in proximity to a first end of said housing for creating said positive air pressure in said air pre-chamber and said second airflow generator is mounted in proximity to a second end of said housing for creating said negative pressure in said air post-chamber.

20. The germicidal treatment system as recited in claim 17 wherein said irradiation source is ultraviolet radiation.

21. The germicidal treatment system as recited in claim 17 wherein said irradiation chamber comprises and irradiation chamber housing, said germicidal treatment system comprises at least one spar or divider situated in said irradiation chamber housing to define a first chamber and a second chamber in said primary chamber so that airflow is directed in a generally U-shaped or V-shaped path, said airflow passing into and through said first chamber in a first direction, around and then into said second chamber where said airflow passes through said second chamber in a second direction that is not co-linear with said first direction.

22. The germicidal treatment system as recited in claim 21 wherein said irradiation chamber comprises a reducer for reducing air velocity and linearity of said airflow as it passes through said irradiation chamber.

23. The germicidal treatment system as recited in claim 22 wherein said reducer comprises a plurality of multitude of discrete, randomly oriented and radiation-transmitting objects situated in at least one of said first chamber or said second chamber.

24. The germicidal treatment system as recited in claim 21 wherein said irradiation chamber housing comprises a first side wall and an opposing second side wall, each of which are generally trapezoidal in shape, said first wall and said second wall coupling said first and second walls to define said irradiation chamber housing, said generally opposing first and second walls being generally inclined relative to each other.

25. The germicidal treatment system as recited in claim 21 wherein said at least one spar or divider divides said primary chamber to provide a first chamber area for receiving airflow from at least one airflow generator, a second chamber area and a joining area for joining said first and second chamber areas, said first and second chamber areas and said joining area cooperating to define said generally U-shaped or V-shaped airflow passageway.

26. The germicidal treatment system as recited in claim 25 wherein said joining area is operatively related and generally opposed to said irradiation source.

27. The germicidal treatment system as recited in claim 17 wherein said irradiation chamber is a one-piece construction and removable mounted in said housing.

28. A germicidal device according to claim 1, said germicidal device wherein:
said at least one airflow generator comprises an intake fan and an exhaust fan;
said intake fan creating a positive pressure in said air pre-chamber; and
said exhaust fan creating a negative pressure or relative vacuum in said air post-chamber;
said germicidal irradiation source irradiating said air stream as it passes into and through said irradiation chamber.

29. The germicidal device as recited in claim 28 wherein said air pre-chamber has a cross-sectional shape that is substantially triangular.

30. The germicidal device as recited in claim 28 wherein said air post-chamber has a cross-sectional shape that is substantially triangular.

31. The germicidal device as recited in claim 28 wherein said germicidal irradiation source is ultraviolet radiation.

* * * * *

UNITED STATES PATENT AND TRADEMARK OFFICE
CERTIFICATE OF CORRECTION

PATENT NO. : 11,052,168 B2
APPLICATION NO. : 15/813506
DATED : July 6, 2021
INVENTOR(S) : David Louis Kirschman It is certified that error appears in the above-identified patent and that said Letters Patent is hereby corrected as shown below:

On the Title Page

Item (73) Assignee, delete "AEROBIOTIX, INC." and insert --AEROBIOTIX, LLC-- therefor.

Signed and Sealed this
Fifteenth Day of November, 2022

Katherine Kelly Vidal
*Director of the United States Patent and Trademark Office*